US006235464B1

(12) United States Patent
Henderson et al.

(10) Patent No.: US 6,235,464 B1
(45) Date of Patent: *May 22, 2001

(54) IMMUNOASSAY ON A PREBLOCKED SOLID SURFACE

(76) Inventors: Glenn L. Henderson, 2908 Red Clay Dr., Apt. 605, Raleigh, NC (US) 27604-3004; Randal A. Hoke, 107 Steel Trap Ct., Cary, NC (US) 27513-4827; Anne C. Hopkins, 105 Seth Ct., Cary, NC (US) 27511-5878; Daniel A. McLaurin, 912 Vickie Dr., Cary, NC (US) 27511-5832

( * ) Notice: Subject to any disclaimer, the term of this patent is extended or adjusted under 35 U.S.C. 154(b) by 0 days.

This patent is subject to a terminal disclaimer.

(21) Appl. No.: 08/326,304

(22) Filed: Oct. 20, 1994

Related U.S. Application Data

(63) Continuation of application No. 07/934,847, filed on Aug. 25, 1992, now abandoned, which is a continuation of application No. 07/272,380, filed on Nov. 17, 1988, now abandoned.

(51) Int. Cl.[7] ........................................ C12Q 1/70
(52) U.S. Cl. .................. 435/5; 435/7.92; 435/975; 436/518; 436/527; 436/531
(58) Field of Search ........................ 435/5, 7.92, 975; 436/518, 527, 531

(56) References Cited

U.S. PATENT DOCUMENTS

| 3,888,629 | * | 6/1975 | Bagshawe ........................ 23/230 B |
| 4,241,175 | * | 12/1980 | Miller et al. ............................. 435/7 |
| 4,342,826 | * | 8/1982 | Cole ........................................ 435/7 |
| 4,372,745 | * | 2/1983 | Mandle et al. ...................... 436/537 |
| 4,459,359 | * | 7/1984 | Neurath ................................ 436/507 |
| 4,659,678 | * | 4/1987 | Forrest et al. ...................... 436/512 |
| 5,208,143 | * | 5/1993 | Henderson et al. ..................... 435/5 |

FOREIGN PATENT DOCUMENTS

WO 84/02193   6/1984 (WO).

\* cited by examiner

*Primary Examiner*—Donna C. Wortman
(74) *Attorney, Agent, or Firm*—Richard E. Brown

(57) ABSTRACT

A method for immunoassay of a viral antigen is performed on a membrane precoated with an inert protein. Nonimmunological capture of antigen takes place by absorption onto the coated membrane. Captured antigen binds to a tracer which includes a label conjugated to a specific antibody, the inert protein concomitantly inhibiting nonspecific binding of tracer. The label may be an enzyme which converts a substrate to a detectable product or converts a blocked inhibitor to an inhibitor whereby a second enzyme is inhibited from converting a substrate to a product. The invention includes a kit of materials for performing an assay in accordance with the method of the invention.

7 Claims, 3 Drawing Sheets

IMMUNOASSAY ON A PREBLOCKED SOLID SURFACE

This application is a continuation of application Ser. No. 07/934,847, filed Aug. 25, 1992, abandoned, which is a continuation of application Ser. No. 07/272,380, filed Nov. 17, 1988, abandoned.

BACKGROUND OF THE INVENTION

1. Field of the Invention

This invention relates to assay for a ligand and materials therein, and, more particularly, relates to an assay including capture of ligand directly on a solid support precoated with a nonspecific agent.

2. Background of the Invention

A variety of assay systems which are both rapid and sensitive has been developed to detect or determine the concentration of a ligand in a liquid. Conventional immunoassays depend on the binding of the ligand to a specific antiligand, and have been particularly useful because they give high levels of specificity and sensitivity. These assays generally employ one of the above reagents in labeled form, the labeled reagent often being referred to as the tracer.

Various means for labeling have been developed. Radioimmunoassay (RIA) procedures use radioisotopes as labels, provide high levels of sensitivity and reproducibility, and are amenable to automation for rapid processing of large numbers of samples. Fluoroimmunoassay (FIA) uses fluorochromes as labels, and provides direct detection of the label by exciting the dye with excitation radiation of appropriate wavelength and detecting fluorescence therefrom.

Enzymes have also been used as labels in immunoassay. In enzyme immunoassay (EIA), the enzyme labeled, reagents are cheap to prepare and are highly stable thus giving a long shelf life, yet yield assays which approach the sensitivity of radioimmunoassay and which give objective results that can be determined either visually or with rather simple equipment, such as a spectrophotometer.

In conventional EIA, an enzyme is covalently conjugated with one component of a specifically binding antigen-antibody pair, and the resulting enzyme conjugate is reacted with a substrate to produce a color which is measured. Often, an unconjugated component, such as an antibody is immobilized on a solid support and serves to capture antigen in a specific binding reaction. Representative of such conventional EIA is U.S. Pat. No. 3,654,090 to Schuurs et al.

Bucher et al. in U.S. Pat. No. 4,588,680 discloses assay for the M protein of various viruses, including Influenza A,B and C viruses. The assay includes disruption of the virus to release the M protein which is absorbed directly onto a polymeric support.

PCT published application WO 86/02733 discloses assay for Herpes simplex virus (HSV) in which antigenic glycoproteins gA/B, gC and gD are absorbed. directly onto a polymeric support or captured by specific monoclonal antibodies on the support.

Sankolli et al. in *Journal of Immunological Methods* 104, 191 (1987) discloses an immunoassay for estradiol in which a solid support is pretreated with a specific anti IgG antibody. This antibody captures specific antiestradiol antibody which in turn captures estradiol and provides an assay of improved reproducibility.

Armstrong et al. in U.S. Pat. No. 4,497,899 discloses an assay for Chlamydia antigen in which the antigen is absorbed directly onto a solid support such as a bead, tube, strip, disk or microtiter plate. The absorbed antigen is then assayed by any conventional EIA, RIA or FIA technique.

In solid phase immunoassay, particularly for large molecular weight molecules, there is often a tendency for materials in the sample being assayed to attach in a nonspecific manner to the solid support. A particular cause of loss of assay sensitivity or irreproducibility is nonspecific absorption of labeled antiligand conjugate (tracer) directly onto binding sites of the solid support which are not filled by antiligand. This problem has conventionally been addressed by blocking unoccupied binding sites, subsequent to application of antiligand, with a protein which does not react with the labeled conjugate. Cole et al., in U.S. Pat. No. 4,407,943, discloses coating a porous membrane with a water insoluble protein, such a zein, affixing an antigen or antibody to the zein layer, and immobilizing an immunochemically neutral protein on the antigen to prevent nonspecific binding of extraneous protein.

While this conventional post blocking has improved assay sensitivity, the sequential application of antiligand and blocking protein to a solid phase prior to ligand binding is cumbersome, time consuming and wasteful of expensive antiligand. Accordingly, there is a need for further improvement in solid phase immunoassay technology, particularly with respect to avoidance of nonspecific binding.

SUMMARY OF THE INVENTION

A method for determining a ligand suspected to be present in a liquid includes contacting the liquid with a solid support having affixed thereto an inert protein and with a trader for the ligand which includes a label whereby the ligand is captured on the support and binds to the tracer. In the present disclosure, the term inert protein means a protein which is immunologically unreactive toward any other component of the assay, with the understanding that the inert protein may well be immunologically reactive toward other materials which are not part of the assay of the invention. After binding, the support is separated from the liquid and the label on the support is detected to indicate the presence of ligand in the liquid. The label may be a radioactive atom, fluorescent dye or enzyme conjugated to an antiligand or encapsulated in a liposome conjugated to the antiligand.

A preferred assay of the invention is a membrane flow-through EIA for a viral antigen in which the label is an enzyme conjugated to an antibody specific for the antigen, and the enzyme label is detected by reaction with a colorless substrate which is converted to a colored product.

An alternate assay format of the invention is a dual enzyme assay for a viral antigen. A hydrolase conjugated to a specific antibody bound to antigen on the support removes a blocking group from a blocked inhibitor to release an inhibitor. The inhibitor inhibits the hydrolysis of an ester substrate to a colored product by an esterase whereby the failure of color to develop is indicative of the presence of the antigen in the liquid.

Another aspect of the invention is a kit of materials useful in performing an assay in accordance with the method of the invention.

Thus, the invention provides an assay for a viral antigen in which substantially all binding sites of a solid support are filled with an inert protein. Antigen capture onto the support containing inert protein is accomplished without a specific capture antibody and thereby avoids the time consuming and labor intensive step of producing specific capture antibody. The inert protein inhibits substantially all nonspecific binding of other protein, including tracer, which would otherwise reduce assay sensitivity. Since the inert protein is readily available and inexpensive, the invention provides a simplified assay of significant cost savings.

DETAILED DESCRIPTION

Figure 1:
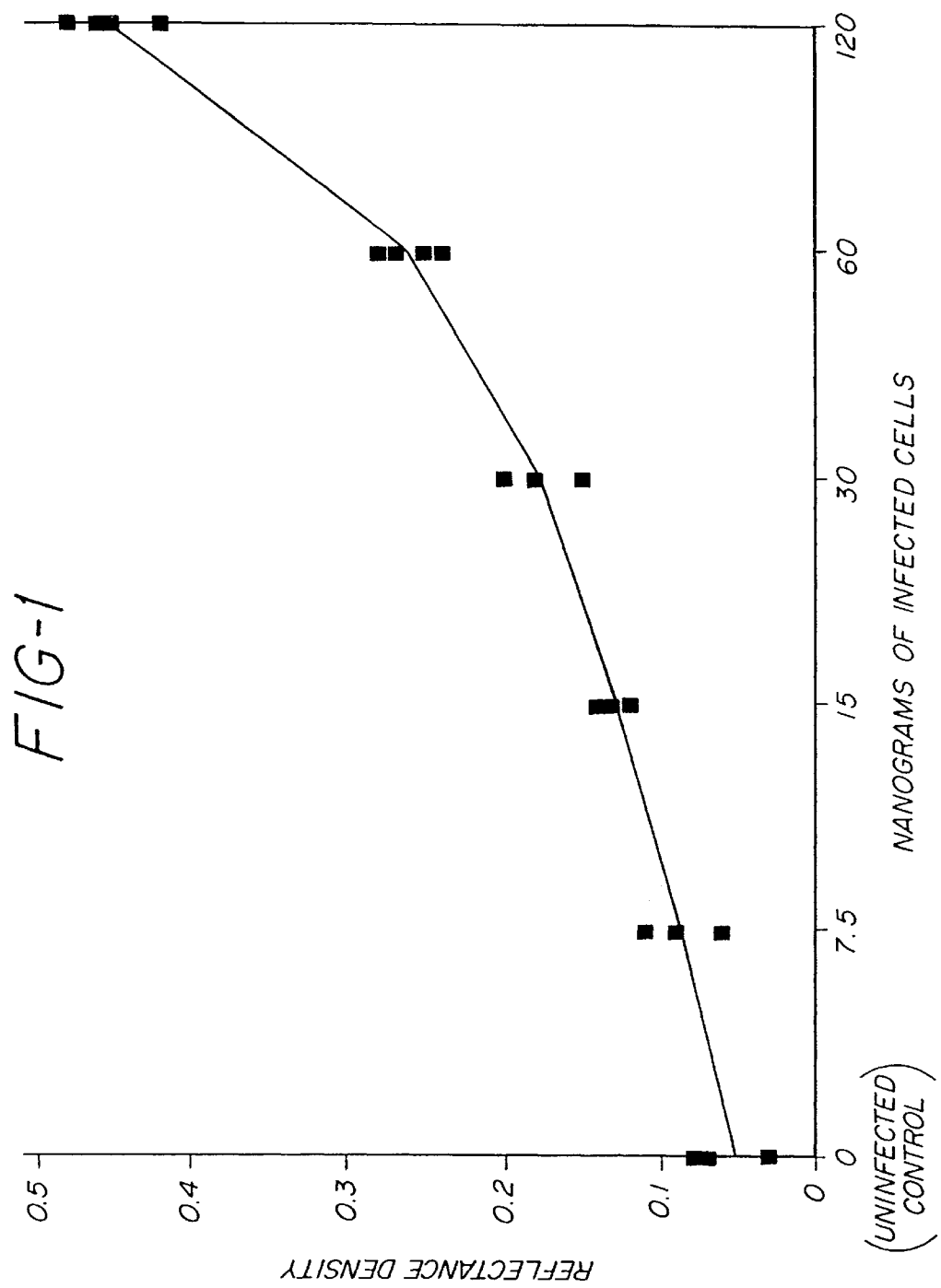
FIGS. 1–3 illustrate the results of assays performed by the method of the invention for RSV, Influenza A and HSV respectively.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

One aspect of the present invention is a method for solid phase immunoassay of a ligand in a liquid sample in which substantially all binding sites on the support are preblocked with a coating of an inert protein. Applicants have discovered that the ligand in the sample to be assayed may be nonimmunologically captured on the coated support in a quantity proportional to its concentration in the sample without reducing the capacity of the inert protein to block all nonspecific absorption of other proteins. The immunoassay of the invention may be configured to detect the presence of ligand in the sample or to determine its concentration, and the term "determined" is intended to mean either qualitative or quantitative ligand assay.

The ligand may be from any source, and may be an antigen, an antibody or a hapten. For example, the ligand may be an antigen present in a body fluid, or it may be isolated from a body fluid and subsequently introduced into a different liquid, such as buffer. In other cases, the ligand may be from a source other than a body fluid, as, for example, a culture of microorganisms or a cellular extract thereof. Preferred ligands are antigens, most preferably viral antigens present in a body fluid, such as Adenovirus, Parainfluenza 3 virus and, most preferably, Herpes simplex virus, HSV, Respiratory syncytial virus, RSV, and Influenza A, Flu A. The invention will hereinafter be described generically in terms of a viral antigen.

Turning now to a detailed description of the assay components, the solid support, as known in the art, may be any support which does not substantially interfere with any other component or step of the assay. Exemplary of solid supports which may be used are glass and polymeric materials, such as polyethylene, polyvinylidene fluoride, polystyrene and the like. Such supports may be fabricated into any suitable shape, such as sheets, tubes, wells microtiter plates, or, most preferably, membranes. Preferred membranes may be of nylon or nitrocellulose. A particularly preferred membrane is a modified nylon membrane commercially available from Pall Corp., Glen Cove, N.Y., under the trade names IMMUNODYNE™ and BIODYNE™ A,B and C.

Any inert protein may be coated onto the membrane which does not interfere with the subsequent binding reaction between antigen and tracer and which does not substantially bind nonspecifically to other proteins in the assay medium. Representative nonlimiting examples of suitable inert proteins are casein and albumin, although others will be evident to those skilled in the art. Coating of the inert protein to the membrane may be carried out by any suitable method, preferably by incubating the membrane with a solution of the protein whereby the protein is physically absorbed into the polymeric matrix of the surface of the membrane.

The membrane having a coating of inert protein is exposed to the sample suspected of containing the viral antigen. Preferably, the coated membrane is incubated with the sample in a transient, flow-through format for about 1 to 15, preferably about 5 minutes at a temperature of about 0 to 50° C., preferably about ambient temperature. By this procedure, antigen in the sample is absorbed onto the coated membrane in proportion to its concentration in the sample. In addition, it has been found that viral antigen is absorbed preferentially even when the sample contains a large excess of extraneous protein, such as is the case when the sample is a body fluid.

The tracer comprises an antibody specific for the antigen having a label conjugated thereto. The label may be any conventional marker which, after binding of the tracer to the antigen captured on the coated support, gives rise to a signal which can be detected. Accordingly, the label may be a radioactive atom or fluorescent dye conjugated to the antibody. When the label is a radioactive element, the signal is radioactive counts. When the label is a fluorescent dye, the signal is fluorescence emission detected after application to the dye of excitation light of suitable wavelength. A typical radiolabel is, for example, $^{127}$I, and a typical fluorescer is, for example, fluorescein isothiocyanate (FITC). Conjugation of radioactive and fluorescent labels to antibodies is conventional and no further details on preparation and use of radio- and fluorescent labels in immunoassay is not needed for a complete understanding of the invention by one skilled in the art.

The preferred tracer of the invention is an antibody having an enzyme conjugated thereto. Any enzyme may be used which may be conjugated to the antibody and for which a substrate convertible to a colored product exists. Suitable enzymes are, for example, cyclases, isomerases and peroxidases. A preferred peroxidase is horseradish peroxidase. Preferred enzymes are hydrolases such as peptidases, esterases, phosphatases and glycosidases. The most preferred tracers include alkaline phosphatase or carboxyesterase conjugated to the antibody. Conjugation of enzymes to antibodies is well-known and fully understood by those skilled in the art.

Alternatively, the radioactive atom, fluorescent dye or enzyme may be encapsulated in a liposome. Encapsulation of labels into liposomes and conjugation of liposomes to antibodies for use as tracers in immunoassay is likewise wholly conventional.

The choice of substrate of course depends on the enzyme component of the tracer and a wide variety of substrates are well-known for each class of enzymes. Preferred substrates are those which form insoluble precipitates on membranes.

When the enzyme is a peroxidase, a preferred substrate is diaminobenzidine. Preferred substrates for hydrolases are indolyl derivatives. For example, when the enzyme is alkaline phosphatase, a preferred substrate is 3-indolyl phosphate. When the enzyme is an esterase, preferred substrates are 3-indolyl acetate and butyrate. These substrates are all well-known in the art.

In accordance with the preferred assay method of the invention, the membrane coated with inert protein and having viral antigen captured thereon, as described above, is incubated with a solution of the tracer in a liquid to induce immunological binding of the antigen and antibody component of the tracer. The membrane having a bound antigen-antibody fraction thereon may then be separated from the liquid phase of the assay medium by any suitable method, preferably by causing the liquid to pass through the membrane. Liquid flow through the membrane may be by gravity or preferably may be enhanced by capillary action induced by absorbent material positioned under the membrane. The membrane may then be suspended in a second liquid such as water, saline or buffer having the enzyme substrate dissolved therein. Enzyme in the bound fraction converts the substrate to a product detectable by a signal associated with color. Thus, the signal detected may be the development or disappearance of a color, or a change from one color to another, or a change in the rate at which the substrate is converted to the product, for example, the color of a substrate may be observed to remain unchanged for a specified length of time. It is preferred that the substrate be colorless until cleaved by the enzyme label to give a colored product. The extent of color formation is proportional to antigen concentration, which may be determined by assaying liquid samples having predetermined quantities of antigen therein and comparing color intensities. Measurements may be made either instrumentally or, preferably with the naked eye.

An alternate assay method of the invention is a dual enzyme assay carried out on the coated support having antigen absorbed thereon. In this embodiment of the assay method, the label may be considered to be a first enzyme which removes a blocking group from a blocked inhibitor. Suitable first enzymes are generally hydrolases, such as phosphatases, peptidases, esterases, glycosidases and the like. Exemplary of, but not limited to, suitable first enzymes are trypsin, thrombin, mammalian liver esterase, acetylcholinesterase, β-galactosidase, or most preferably, alkaline phosphatase.

The blocked inhibitor may be any material which may be converted by the first enzyme to an inhibitor a the second enzyme. The preferred blocked inhibitor has two components, the inhibitor and the blocking group and is unreactive toward the second enzyme until its blocking group is removed by the first enzyme and the inhibitor is liberated into the assay medium. Thus, the choice of the components of the blocked inhibitor depends on the first and second enzymes to be used. The blocking group should be one which can be covalently conjugated to the inhibitor by a bond which can be cleaved substantially selectively by the first enzyme, and the inhibitor component should inhibit the activity of the second enzyme while having substantially no effect on, the first enzyme. Thus, the nature of the second enzyme and its substrate will be discussed prior to further description of the blocked inhibitor and the inhibitor.

The second enzyme of the dual enzyme assay is generally a hydrolase which converts the substrate to a product detectable by a signal associated with color. It is preferred that the second enzyme is substantially unreactive toward the blocked inhibitor. Suitable hydrolases are, for example, phosphatases, peptidases such as trypsin, chymotrypsin and pepsin, or preferably esterases such as acetyl cholinesterase (AChE) and butyl cholinesterase. The most preferred second enzyme is a carboxyesterase, such as pig or rabbit liver esterase (RLE) wherein the preferred substrate is an indolyl ester.

As mentioned above, the first enzyme component of the tracer cleaves the blocking group from the blocked inhibitor to provide the inhibitor of the second enzyme. Suitable inhibitors and blocked enzyme inhibitors are illustrated by the general formula I set forth below, wherein the nature of group B, as described later, determines whether the compound is an inhibitor or a blocked inhibitor:

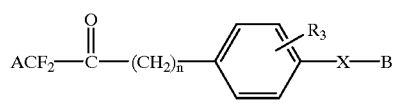

I

In formula I $R_1$ may be H, lower alkyl of 1–6 carbon atoms, branched or unbranched, nitro, alkoxy, halogen and the like; X may be O, S or $NR_2$ wherein $R_2$ may be H or lower alkyl of 1–6 carbon atoms; n may be 1–6; A may be F or $CF_3$; and B may be H, a phosphoric acid or salt, a glycosyl group, an amino acid residue, such as a lysine or arginine residue covalently conjugated to X through the amino acid carboxyl group, an acyl group of 2–4 carbon atoms such as an acetyl or butyryl group, or a peptide of the formula II

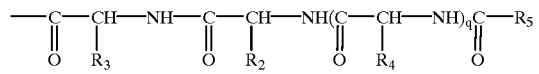

II

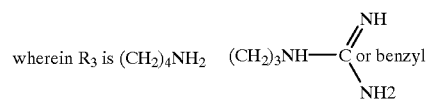

$R_4$ may be H, lower alkyl or hydroxy-lower alkyl of 1 to 4 carbon atoms, branched or unbranched, $CH_2COOH$ or $(CH_2)_2COOH$; $R_5$ may be lower alkyl or lower alkoxy of 1 to 4 carbon atoms, branched or unbranched, phenyl, or benzyloxy; and q may be 0–10.

When B is H, formula I represents enzyme inhibitors. When B is any group other than H, formula I represents blocked enzyme inhibitors. When B is a phosphoric acid or salt thereof, it is intended that B have the formula III

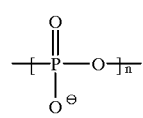

III wherein P is bonded to X and n may be as described above.

The inhibitor and blocked inhibitor in accordance with formula I may be synthesized by any sequence of conventional chemical reactions as may be envisioned by one skilled in the art. Suitable and convenient methods are given in the Examples, below. The following list of effective enzyme inhibitors is intended to be exemplary only.

| Name | omr data | $K_i$ (M)^ (Esterase) |
|---|---|---|
| 1. 1,1,1-trifluoro-3-(4-hydroxy-phenyl)propanone | (CDC13) - 3.91(s, 2H), 5.21(bs, 1H), 6.90(d, 2H), 7.10(d, 2H) | $2.0 \times 10$-6, RLE |
| 2. 1,1,1-trifluoro-3-(3-hydroxy phenyl)-2-propanone | (CDC13) - 4.00(s, 2H), 4.80(bs, 1H), 6.80(m, 3H), 7.30(m, 1H) | >10-4, PLE |
| 3. 1,1,1-trifluoro-4-(4-hydroxy-phenyl)-2-butanone | (CDC13) - 2.95(m, 4H), 4.90(bs, 1H), 6.92(dd, 4H)J = 4, 60 Hz | $2.0 \times 10$-8, RLE |
| 4. 1,1,1-trifluoro-4-(3-hydroxy-phenyl)-2-butanone | (CDC13) - 2.94(t, 2H), 3.05(t, 2H), 5.70(bs, 1H), 6.80(m, 3H), 7.15(m1H) | $1.0 \times 10$-7, RLE |
| 5. 1,1,1-trifluoro-5-(4-hydroxy-phenyl)-2-pentanone | (CDC13) - 1.91(t, 2H), 2.59(t, 2H), 2.68(t, 2H), 5.23(bs, 1H), 6.95(d, 2H), 7.10(d, 2H) | $1.0 \times 10$-8, RLE |
| 6. 1,1,1-trifluoro-5-(3-hydroxy-phenyl)-2-pentanone | (CDC13) - 1.95(p, 2H), 2.70(t, 2H), 2.95(t, 2H), 5.40(bs, 1H), 6.70(m, 3H), 7.30(m, 1H) | $1.7 \times 10$-7, RLE |
| 7. 1,1,1-trifluoro-6-(4-hydroxy-phenyl)-2-hexanone | (CDC13) - 1.63(m, 4H), 2.59(q, 2H), 2.70(q, 2H), 5.55(bs, 1H), 6.77(d, 2H) 7.02(d, 2H) | $2.0 \times 10$-8, RLE |
| 8. 1,1,1,2,2-pentafluoro-5-(4-hydroxy-phenyl)-3-pentanone | (CDC13) - 2.94(m, 2H), 3.04(m, 2H), 4.75(bs, 1H), 6.90(d, 2H), 7.10(m, 2H) | $8.0 \times 10$-7, RLE |

^PLE, Pig Liver Esterase (E.C. 3.1.1.1)
RLE, Rabbit Liver Esterase (E.C. 3.1.1.1)

Another aspect of the invention is a reagent kit or package of materials for performing an assay for a ligand in accordance with the method of the invention. The kit may include a solid support, preferably a membrane, coated with an inert protein, an antiligand, an enzyme conjugated to the antiligand, and a substrate for an enzyme. The kit may also include a second enzyme, and a blocked inhibitor of the second enzyme, standards for the ligand, as, for example, one or more ligand samples of known concentration, or it may include other reagents, enzyme substrates, or other labeled or unlabeled specific ligands, antiligands or complexes thereof useful in carrying out the assay. It may include solutions, such as saline or buffers. The components of the kit may be assembled in a housing, preferably plastic, containing a material positioned under the membrane, such as absorbent paper, to facilitate flow of assay liquids through the membranes by capillary action.

EXPERIMENTAL

Routine Analytical Techniques—Flash Silica gel chromatography was performed on ICN silica gel 32–63 mesh at 3–7 psi. Analytical TLC was performed on 0.25 mm 5×20 cm aluminum-backed silica gel plates from EM Scientific. Preparative TLC was performed on 2.0 mm 20×20 cm glass-back silica gel plates from EM Scientific. Melting points were performed on a Thomas Hoover capillary melting point apparatus and are uncorrected. NMR spectra were recorded on an IBM WP-200SY spectrophotometer and chemical shifts are reported in ppm relative to trimethylsilane. HPLC was performed on a Waters 510 two pump system with UV detection using one of two solvent systems on a Brownlee AX- 300 7×250 mm column. (System A) initial hold for 5 minutes at 30 mM NH4OAc pH 6.5 followed by a linear gradient to 2.0 M NH4OAc over a 30 minute period followed by a hold at 1.0 M NH40Ac for 5 minutes. System B) used an isocratic buffer system of 30 mM NH4OAc pH 6.5 for 40 minutes. Flow rates were 1.0 mL/minute. Gas chromatography was performed on a H.P. 5840A Gas Chromatograph equipped with a FID and an automatic injector using a 30 M DB-1 Megabore column purchased from J&W Scientific, Inc. GC conditions were as follows: A three minute hold at 100° C. followed by a 10° C./minute gradient to 250° C. followed by a 3.0 minute hold at 250° C. at 16.0 mL/minute flow rate.

Inhibition constants were measured in 50 mM Tris pH=8.0. Enzyme and inhibitor were incubated at ambient temperature for 20 minutes. Substrate for the enzyme was then added and the rate of hydrolysis was followed spectrophotometrically. The substrate for PLE and RLE was o-nitro-phenylbutrate and for AChE was acetyl thiocholine and Ellman's reagent.

The following examples are provided to further describe the invention but are not to be considered in any way as limitative of the invention.

EXAMPLE I

Diammonium [4-(3-oxo-4,4,4-trifluorobutyl)phenyl] phosphate

A. Preparation of Ethyl 2-(4-methoxybenzyl)-3-oxo-4,4,4-trifluorobutanoate

A 1 L four neck round bottom flask, fitted with reflux condenser, dropping funnel, argon inlet, and magnetic stirrer was charged with 7.17 g (0.149 mol) of a 50% (w/v) oil dispersion of sodium hydride and 300 mL of dry ethyl ether. Absolute ethanol (9.0 mL) was slowly added to the stirred solution. After the evolution of hydrogen stopped, a mixture of 25 g (0.136 mol) of ethyl 4,4,4-trifluoroacetoacetate and 21.3 g (0.136 mol) of 4-methoxybenzyl chloride was added over a 1 hour period. The resulting mixture was refluxed overnight, cooled, extracted with water, 1 N hydrochloric acid, dried over anhydrous magnesium sulfate and rotary-evaporated under reduced pressure. The crude reaction mixture (33.5 g) was chromatographed on a 60 mm xx 300 mm silica gel column with ethyl acetate/hexane (25/75). Similar fractions were combined and gave 9.4 g (23%) of the (spectroscopically complex) product as an oil. NMR (CDC13): 1.26(m,3H), 3.77(s,3H), 4.12(m,2H), 7.08(m, 2H).

B. Preparation of 1,1,1-trifluoro-4-(4-hydroxy-phenyl)-butan-2-one

A 100 mL round bottom flask, fitted with reflux condenser, magnetic stirrer and argon inlet was charged with 2.05 g (6.7 mmol) of ethyl 2-(4-methoxy-benzyl)-3-oxo-4,4,4-trifluorobutanbate. (I), 20 mL of 31% (w/v) hydrogen bromide in acetic acid, and 10 mL of water. This mixture -was heated'overnight at 120° C., cooled, concentrated under reduced pressure and partitioned between dichloromethane and water. The organic layer was extracted sequentially with aqueous bisulfite, and saturated sodium bicarbonate, and then dried over anhydrous magnesium sulfate. Solvent was removed under reduced pressure. The crude reaction mixture was chromatographed on a 50 mm×300 mm silica gel column with ethyl acetate/hexane (50/50). Similar fractions were combined and the solvent was removed under reduced pressure to yield 600 mg (41%) as a clear oil. NMR(CDC13): 2.95(m,4H), 5.40(bs, 1H), 6.93(dd,4H) J=4, 60 Hz.

C. Preparation of diethyl [4-(3-oxo-4,4,4-tri-fluorobutyl) phenyl] phosphate

A 10 mL round bottom flask, fitted with argon inlet and magnetic stirrer was charged with 400 mg (1.8 mmol) of 1,1,1-trifluoro-4-(4-hydroxyphenyl)-butan-2-one, 400 mg (2.3 mmol) of diethyl chlorophosphate, 0.15 mL of dry pyridine and 5 mL of dichloromethane. The reaction mixture was stirred overnight at ambient temperature, filtered to remove pyridinium hydrochloride, extracted with 0.2 N hydrochloric acid, extracted with water, and dried over anhydrous magnesium sulfate. Solvent removal under reduced pressure afforded a crude yield of 600 mg of a brown oil. Two hundred mg (31%) of a clear oil was isolated from a preparative TLC plate developed with ethyl acetate/hexane (50/50). NMR(CDC13): 1.50(m6H), 3.0(m,4H), 4.20(m,4H), 7.15(s,4H).

D. Preparation of diammonium [4-(3-oxo-4,4,4-tri-fluorobutyl)phenyl] phosphate

A 25 mL one neck round bottom flask, fitted with argon inlet and magnetic stirrer was charged with 5.0 mL of dichloromethane, 140 mg (0.40 mmol) of diethyl [4-(3-oxo-4,4,4-trifluorobutyl)phenyl] phosphate (III) and 2.0 mL of bromotrimethylsilane. After stirring this mixture for 3 hours at ambient temperature, 10 mL of methanol was added and the volatile materials were removed under reduced pressure. The residue was dissolved in water and adjusted to pH 7.0 with 1.0 N sodium hydroxide. The aqueous solution was extracted with diethyl ether and lyophilized to give 190 mg of a white solid. This material was dissolved in 10 mL of water, and purified by anion exchange HPLC. Gradient conditions: initial hold for 5 minutes at 20 mM ammonium acetate, pH 6.5; followed by a linear ramp to 1.0 M ammonium acetate over a 20 minute period; followed by a hold at 1.0 M ammonium acetate for 15 minutes. At a flow rate of 2.5 mL/min, the product eluted at approximately 32 minutes. Column capacity was 20 mg. Product fractions from several HPLC runs were pooled and lyophilized to yield 50 mg (37%). mp 235–240° C. NMR (D20): 1.90(m, 2H), 2.56(m,2H), 4.65(s, DOH), 6.88(dd,4H) J=6, 82 Hz.

EXAMPLE II

Assay for Respiratory Syncytial Virus (RSV)

A membrane filter stack was assembled with the following configuration:

| Top layer | Three micron IMMUNODYNE ™ Immunoaffinity Membrane, (Pall, East Hills, New York, #BIA0030HC5). Precoated by immersion in phosphate buffered saline containing 0.3% casein for 30 minutes at ambient temperature. |
|---|---|
| Next layer | Non-woven rayon sheet (Schleicher and Schuell, Keene, New Hampshire; #5-S). |
| Bottom layer | Cellulose absorbent pads (2) (Filtration Sciences, Mount Holly Springs, Pennsylvania; #ED 320-200) |

The membrane layers were encased in a plastic holder which includes a receiving well formed above the top layer. Within this well was fitted a flow restriction insert which has an aperture more narrow than the receiving well and sits flush against the top membrane.

An antigen stock was prepared with respiratory syncytial virus (RSV) (Long strain) infected HEp-2 cells diluted in a buffer containing: 250 mM tris(hydroxymethyl) aminomethane hydrochloride (Tris HCl), 150 mM sodium chloride (NaCl), 10 mM ethylene-diaminetetraacetate (EDTA), 4% (v/v) polyoxyethylene sorbitan monolaurate (Tween 20), 1% n-acetyl-cysteine, 0.2% sodium azide ($NaN_3$), pH 8.5. Control antigen was prepared in a similar manner from uninfected HEp-2. cells.

A 150 $\mu$L aliquot of this antigen (or control) was applied to the device and allowed to drain through the flow restriction insert and onto the top membrane layer. (Liquid is drawn through the top membrane by the capillary action of the supporting absorbent layers.) The flow restriction insert was then removed, and to the device was added 150 $\mu$L of a wash solution consisting of 50 mM Tris HCl, 150 mM NaCl, 0.2% $NaN_3$, pH 7.2 (Tris buffered saline (TBS)), additionally containing 1 mg/mL of rabbit IgG.

A solution containing 27 $\mu$g/mL of anti-RSV antibody conjugated to alkaline phosphatase was prepared in a buffer containing 50 mM Tris HCl, 100 mM NaCl, 200 mM sodium phosphate, 1% casein, 1 mM magnesium chloride, 0.1 mM zinc chloride, and 1 mM 2-mercaptoethanol, pH 7.5. A 150 $\mu$L aliquot of this mixture was added to the device and allowed to absorb into the membrane stack. Following a brief (two minute) incubation, the device was washed with 300 $\mu$L of TBS (without IgG).

A 150 $\mu$L solution containing 0.33 mg/mL nitroblue tetrazolium, 1% methanol, and 0.2% $NaN_3$ was added to the device. This was followed by the addition of 150 $\mu$L of a solution containing 12 mM levamisole in 50 mM 2-amino-2-methyl-1-propanol acetate (AMP HOAc), 0.2% $NaN_3$, 19 mM magnesium chloride, at pH 9.8. Following a five minute incubation at ambient temperature, the color forming reaction was stopped by the addition of 150 μL of a solution containing 200 mM potassium phosphate, 10 mM EDTA, 0.2% NaN$_3$, pH 7.2.

The color density of the resulting membrane was measured with a reflectance densitometer (Gretag, Seattle, Wash., model 183). The results of an experiment performed with a series of antigen dilutions are presented in the FIG. 1.

EXAMPLE III

Assay for Influenza Virus, Type A

An assay for influenza virus was performed in a manner similar to Example II with the following exceptions:

1) The antigen stock was prepared from Madin-Darby canine kidney (MDCK) cells infected with Influenza A (WSN strain).
2) Top layer membrane was 3 micron Biodyne C (Pall, East Hills, N.Y.; #BNPCH5) instead of Immunodyne.
3) Antigen stock buffer was prepared with Tris acetate instead of Tris hydrochloride, contained no sodium chloride, and additionally contained 1 mM ethylene bis(oxyethylenenitrilo)tetra-acetic acid (EGTA).
4) The conjugate diluent contained 100 mM instead of 50 mM Tris, and 150 mM instead of 100 mM NaCl.
5) Levamisole concentration was 16 mM instead of 12 mM.

Figure 2:
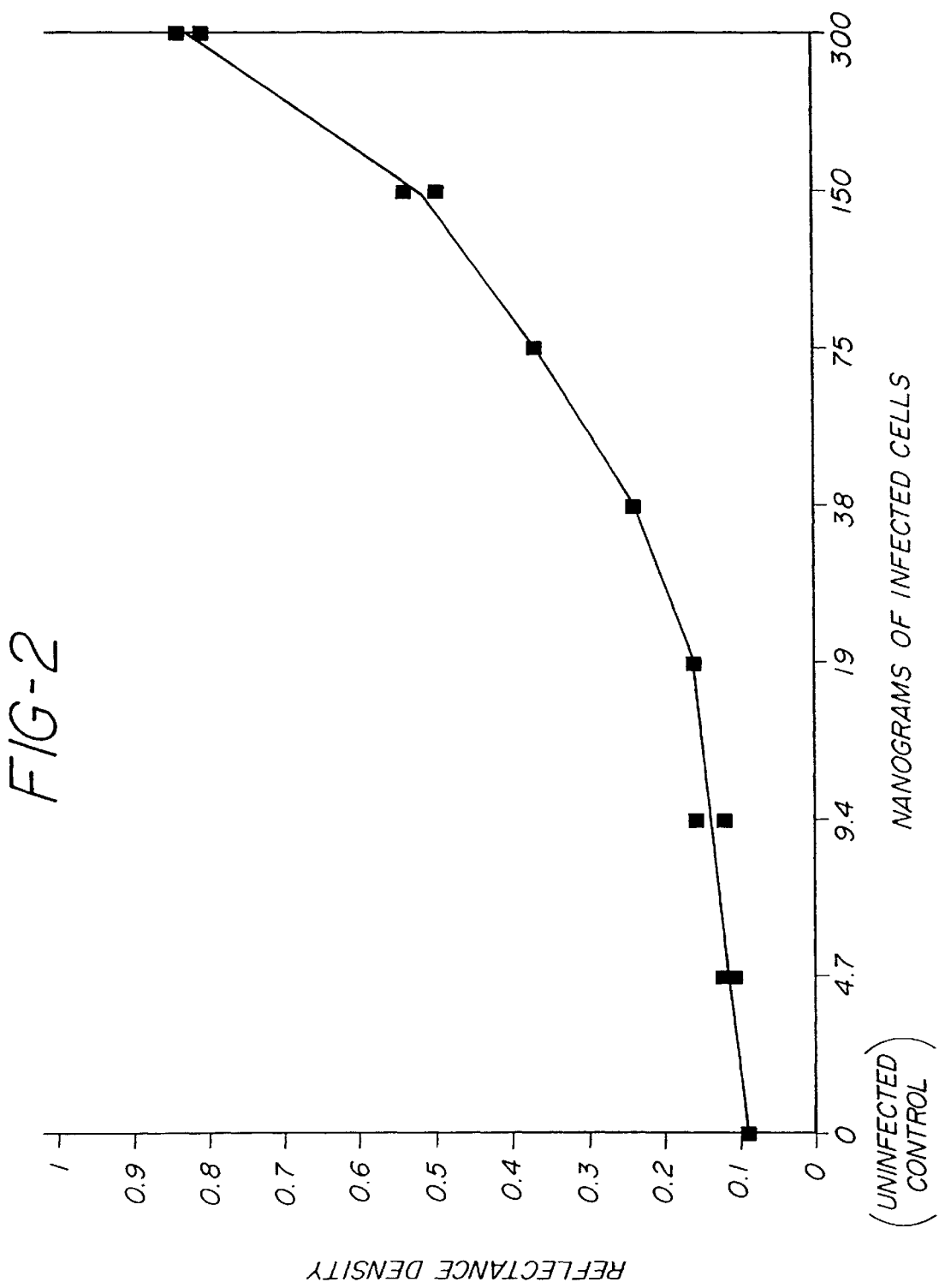

The results of an experiment performed with a series of antigen dilutions are presented in FIG. 2.

EXAMPLE IV

Assay for Herpes Simplex Virus (HSV)

An assay for herpes simplex virus (type I and II) was performed in a manner similar to the Example II with the following exceptions:

1) The antigen stock was prepared from Vero cells infected with HSV type II.

Figure 3:
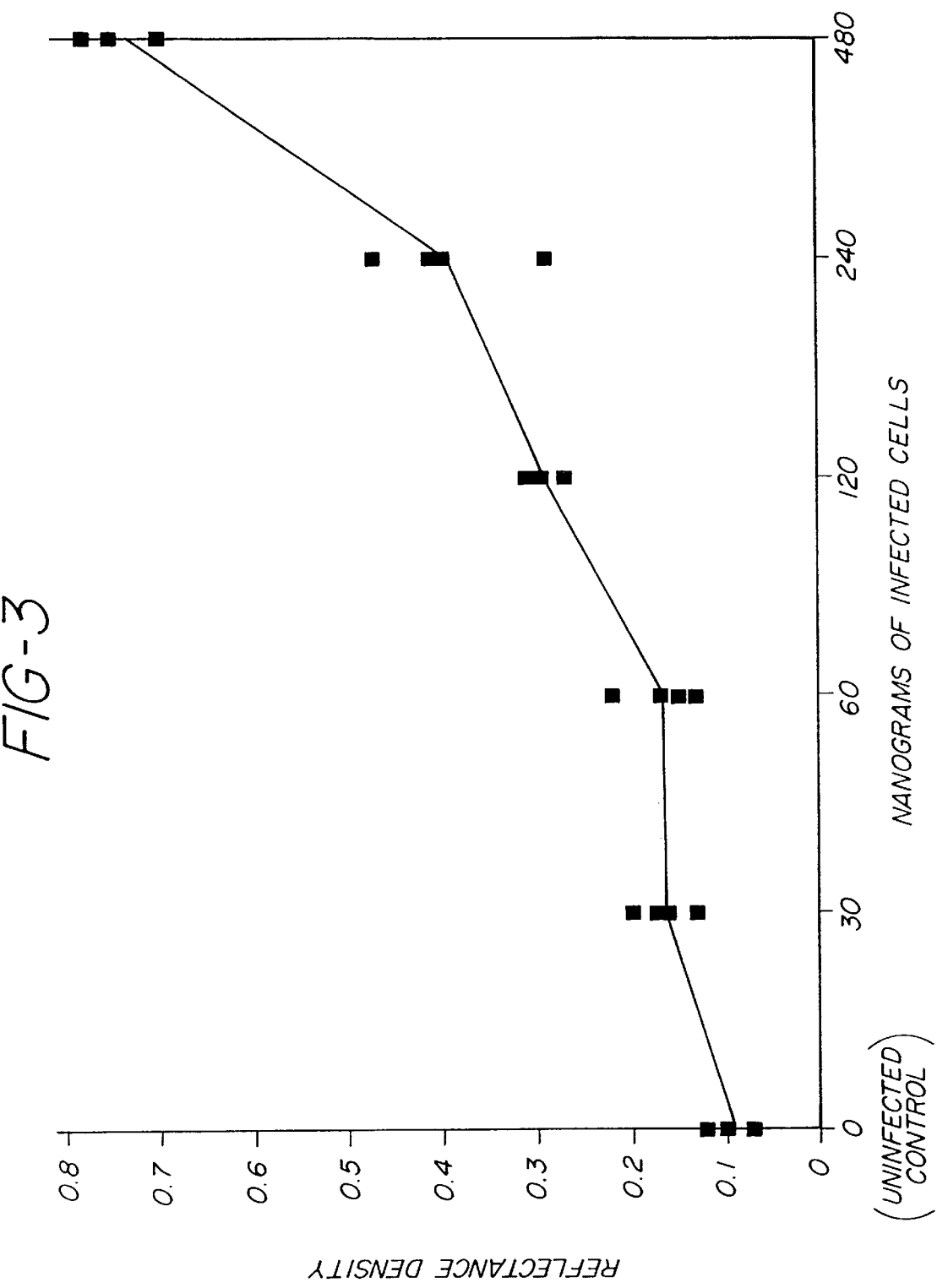

The results of an experiment performed with a series of antigen dilutions are presented in FIG. 3.

EXAMPLE V

Dual Enzyme Cascade Assay for Respiratory Syncytial Virus (RSV)

A dual enzyme cascade assay for RSV is performed in a manner similar to Example II with the following exceptions:

1) Rabbit liver carboxyesterase is coated on the surface of an Immunodyne Immuno-affinity membrane. The membrane is then blocked with casein in the previously described manner.
2) Following the application of the alkaline phosphatase-antibody conjugate and subsequent wash, a solution of 0.15 mM masked inhibitor (4-(3-oxo-4,4,4-trifluorobutyl)phenyl phosphate) is 50 mM diethanolamine, pH 9.0 is added to the device. This solution is allowed to incubate at ambient temperature for 20 minutes. A chromogenic solution containing 0.5 mM 3-indolyl butyrate (Research Organics, Cleveland, Ohio) in TBS is then added to the device. Color development is stopped after a suitable period by the addition of 1 mM 1,1,1-tri-fluoroacetophenone (Aldrich, Milwaukee, Wis.). Color density is measured with a reflectance densitometer as described in the previous example.

The color density of the unknown sample is compared with an uninfected control. If the unknown appears significantly lighter than the control (less than half the reflectance density of the control) then it is judged to be a positive result, indicating the presence of viral material.

Thus, the invention provides an assay for a viral antigen which does not include a specific capture antibody for the antigen. Instead, a solid support is precoated with an inert protein and antigen is captured directly on the coated support. Further, the inert protein, even though applied as a precoat prior to antigen capture, prevents substantially all nonspecific binding of other proteins, such as tracer, which would otherwise reduce assay sensitivity.

What is claimed is:

1. A method for assay of a viral antigen in an aqueous liquid comprising:
    a) combining a first aqueous liquid suspected of containing a viral antigen to be detected with a membrane precoated with albumin or casein but not with a specific capture antibody whereby said antigen is nonimmunologically absorbed onto the precoated membrane;
    b) separating said membrane from said first liquid by causing said first liquid to pass through said membrane;
    c) incubating said membrane having said viral antigen to be detected absorbed thereon with a tracer comprising an antibody and an enzyme selected from the group consisting of a cyclase, isomerase, peroxidase and hydrolase whereby said viral antigen to be detected absorbed on said precoated membrane binds to said tracer to give a bound fraction including said enzyme on said membrane;
    d) passing a second aqueous liquid containing a substrate for said enzyme through said membrane, said substrate being converted by said enzyme on said membrane to a colored product; and
    e) detecting said viral antigen by a signal associated with the color of said product.

2. The method of claim 1 wherein said viral antigen is selected from the group consisting of Herpes simplex virus, Respiratory syncytial virus and Influenza A virus.

3. The method of claim 1 wherein said hydrolase is selected from the group consisting of a peptidase, esterase, phosphatase and glycosidase.

4. The method of claim 1 wherein said tracer further comprises a liposome having said enzyme encapsulated therein, said liposome being conjugated to said antibody.

5. A kit of materials for performing an assay for a viral antigen comprising a membrane precoated with albumin or casin but not with a specific capture antibody, an antibody for the antigen to be detected having an enzyme conjugated thereto, a housing containing an absorbent material positioned adjacent said membrane, and a substrate for said enzyme, said enzyme being selected from the group consisting of a cyclase, isomerase, peroxidase and hydrolase.

6. The kit of claim 5 further comprising at least one other reagent selected from the group consisting of buffer, saline and at least one liquid containing viral antigen of known concentration.

7. The kit of claim 5 further comprising one or more containers.

* * * * *